United States Patent [19]
Nicks et al.

[11] Patent Number: 5,637,864
[45] Date of Patent: Jun. 10, 1997

[54] OPTICAL INSPECTION OF TRANSLUCENT CONTAINERS FOR VERTICAL CHECKS AND SPLIT SEAMS IN THE CONTAINER SIDEWALLS

[75] Inventors: Timothy J. Nicks; James A. Ringlien, both of Maumee, Ohio

[73] Assignee: Owens-Brockway Glass Container Inc., Toledo, Ohio

[21] Appl. No.: 389,343

[22] Filed: Feb. 15, 1995

Related U.S. Application Data

[63] Continuation of Ser. No. 122,843, Sep. 17, 1994, abandoned.

[51] Int. Cl.$^6$ .................................................. G01N 9/04
[52] U.S. Cl. ........................... 250/223 B; 356/240
[58] Field of Search ................ 250/223 B, 227.21, 250/227.24; 356/240, 239; 209/526

[56] References Cited

U.S. PATENT DOCUMENTS

| | | | |
|---|---|---|---|
| 3,549,890 | 12/1970 | Keller | 250/209 |
| 3,588,258 | 6/1971 | Sendt | 250/223 B |
| 3,639,067 | 2/1972 | Stephens | 250/223 B |
| 3,687,559 | 8/1972 | Fischer | 250/223 B |
| 3,987,301 | 10/1976 | O'Conner | 250/223 B |
| 4,055,834 | 10/1977 | Planke | 250/223 B |
| 4,411,522 | 10/1983 | O'Connor et al. | 356/240 |
| 4,584,469 | 4/1986 | Lovalenti | 250/223 B |
| 4,751,386 | 6/1988 | Gardner | 250/223 |
| 4,808,813 | 2/1989 | Champeiter | 250/227 |
| 4,919,534 | 4/1990 | Reed | 250/223 B |
| 4,975,568 | 12/1990 | Taniguchi et al. | 250/223 |
| 5,020,908 | 6/1991 | Hermann | 356/239 |
| 5,258,611 | 11/1993 | Leser | 356/240 |
| 5,270,535 | 12/1993 | Leser | 356/240 |

FOREIGN PATENT DOCUMENTS

| | | |
|---|---|---|
| 1369597 | 7/1964 | France . |
| 55104744 | 8/1980 | Japan . |
| 1115542 | 5/1968 | United Kingdom . |
| 2133538 | 7/1984 | United Kingdom . |

*Primary Examiner*—Stephone B. Allen

[57] ABSTRACT

Apparatus for detecting checks in the sidewall of a translucent container that includes a light source for illuminating an elongated strip of the container sidewall parallel to the central axis of the container in such a way that illumination rays are incident at any point of the strip from multiple differing angles. A camera is positioned externally of the container for receiving light reflected by checks in the illuminated strip, and electronic circuitry is coupled to the camera for detecting checks in the container as a function of such reflected light. Since the light rays at any point in the elongated illuminated strip on the container sidewall are incident from multiple differing angles, planar checks in the container sidewall that are not precisely vertical in orientation will have a greater chance of reflecting light energy from the source onto the detector.

13 Claims, 2 Drawing Sheets

OPTICAL INSPECTION OF TRANSLUCENT CONTAINERS FOR VERTICAL CHECKS AND SPLIT SEAMS IN THE CONTAINER SIDEWALLS

This is a continuation of application Ser. No. 08/122,843 filed Sep. 17, 1994, now abandoned.

The present invention is directed to optical inspection of translucent containers, and more specifically to an apparatus and method for detecting so-called vertical checks and split seams in the sidewalls of translucent containers.

BACKGROUND AND OBJECTS OF THE INVENTION

In the manufacture of translucent containers such as clear or colored glass bottles, various types of checks or other commercial variations can occur in the sidewalls of the containers. For example, variations known as split seams and vertical checks may be present in the sidewall of a container. These split seams and vertical checks are mirror-like reflective cracks that lie in a plane and extend generally radially from the longitudinal axis of the container. Many devices have been proposed for detecting such variations.

U.S. Pat. No. 4,584,469 discloses a device for detecting split seams and vertical checks in the sidewall of a glass container. A light source is positioned to one side of the container to direct light energy onto the container wall from a direction perpendicular and lateral to the container axis. The light source comprises an incandescent bulb and a cylindrical lens for projecting an image of the bulb filament onto the container sidewall in an elongated narrow tightly focused strip parallel to the container axis. A linear array camera is positioned to receive an image of the illuminated portion of the container from a direction perpendicular to the illumination and container axes. As the container is held in position and rotated about its axis, a radial planar check will eventually be rotated into a position to reflect light from the source to the detector. Thus, the vertical check or split seam is detected as a bright spot on what is otherwise a normally gray or dark background viewed by the detector. (Directional terms such as "vertical" assume vertical orientation of the container axis with the mouth opening upwardly, as is typical in the container inspection art.)

Although the device disclosed in the noted patent has enjoyed substantial commercial success, further improvements remain desirable. In particular, the device disclosed in the noted patent is limited in its ability to detect checks that are not precisely vertical and parallel to the container axis. That is, if a check is non-vertical, light incident on the check will be reflected by the check but not necessarily incident on the camera. It is therefore a general object of the present invention to provide an apparatus and method of the general character or type disclosed in the above-noted patent having enhanced ability to detect and inspect non-vertical radial checks (and split seams) in the container sidewall.

SUMMARY OF THE INVENTION

Apparatus for detecting checks in the sidewall of a translucent container in accordance with a presently preferred embodiment of the invention includes a light source for illuminating an elongated strip of the container sidewall parallel to the central axis of the container in such a way that illumination rays are incident at any point of the strip from multiple differing angles. A camera is positioned externally of the container for receiving light reflected by checks in the illuminated strip, and electronic circuitry is coupled to the camera for detecting checks in the container as a function of such reflected light. Since the light rays at any point in the elongated illuminated strip on the container sidewall are incident from multiple differing angles, as distinguished from substantially unidirectional illumination in the above-noted patent, planar checks in the container sidewall that are not precisely vertical in orientation will have a greater chance of reflecting light energy from the source onto the detector.

In the preferred embodiment of the invention herein disclosed, the light source comprises a fiber-optic ribbon having ends disposed in an essentially linear array optically parallel to the container axis, and a cylindrical lens disposed between the fiber-optic ribbon array and the container for focusing light from the array in a direction perpendicular to the container axis to form the narrow elongated illumination strip. In this way, the light rays incident on the container sidewall are oriented at multiple angles essentially in a plane parallel to the container axis. The fiber-optic ribbon has a dimension parallel to the central axis of the container at least as great as the longitudinal dimension of the illuminated strip. The camera preferably comprises a linear array of light sensitive elements optically parallel to the container axis and the illuminated strip, with the camera array being scanned by detection electronics at increments of container rotation.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENT

Figure 1:
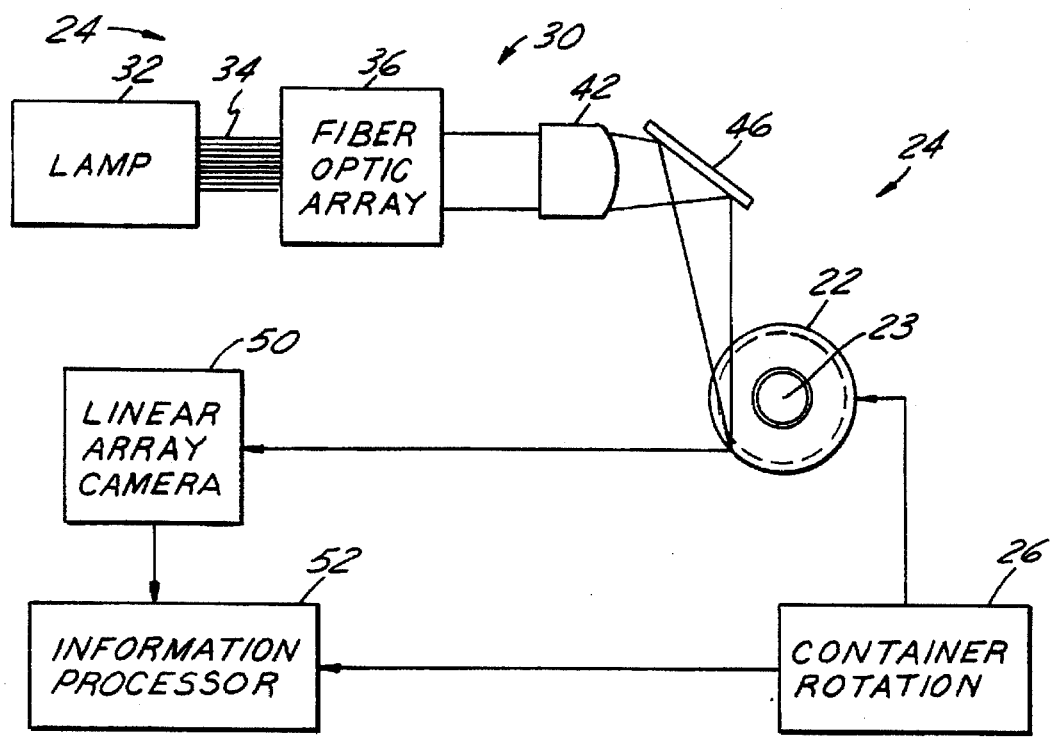
FIG. 1 is a functional block diagram of apparatus for inspecting translucent containers in accordance with the present invention.

Referring to the drawings, a conveyor 20, typically including a starwheel (not shown) and a slide plate 21, is so disposed and connected to a source of molded containers as to bring successive containers 22 into position at an inspection station 24. Conveyor 20 may be of any suitable type, such as those shown in U.S. Pat. Nos. 4,230,219 and 4,378,493 as well as above-noted U.S. Pat. No. 4,584,469, and would typically include a rotatable starwheel for bringing successive containers into position and holding the containers in fixed position during the scanning operation. A container rotating device 26, such as a drive roller, is positioned to engage container 22 at station 24 and to rotate the container about its central axis 23. An encoder or the like is coupled the container rotation mechanism to provide signals indicative of increments of container rotation. Alternatively, with the container rotating at constant speed, increments of container rotation may be inferred by increments of time.

Figure 3:
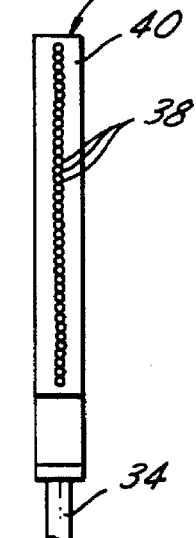
FIG. 3 is an end elevational view of a portion of the light source taken substantially along the line 3—3 in FIG. 2.
Figure 4:
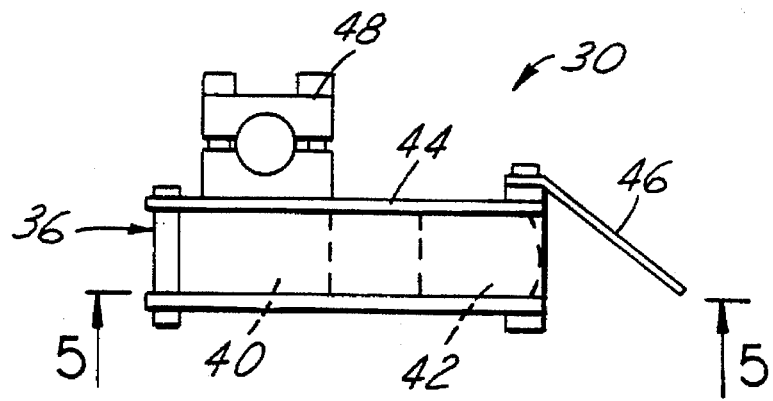
FIG. 4 is a top plan view of a portion of the light source illustrated in FIGS. 1–3.
Figure 5:
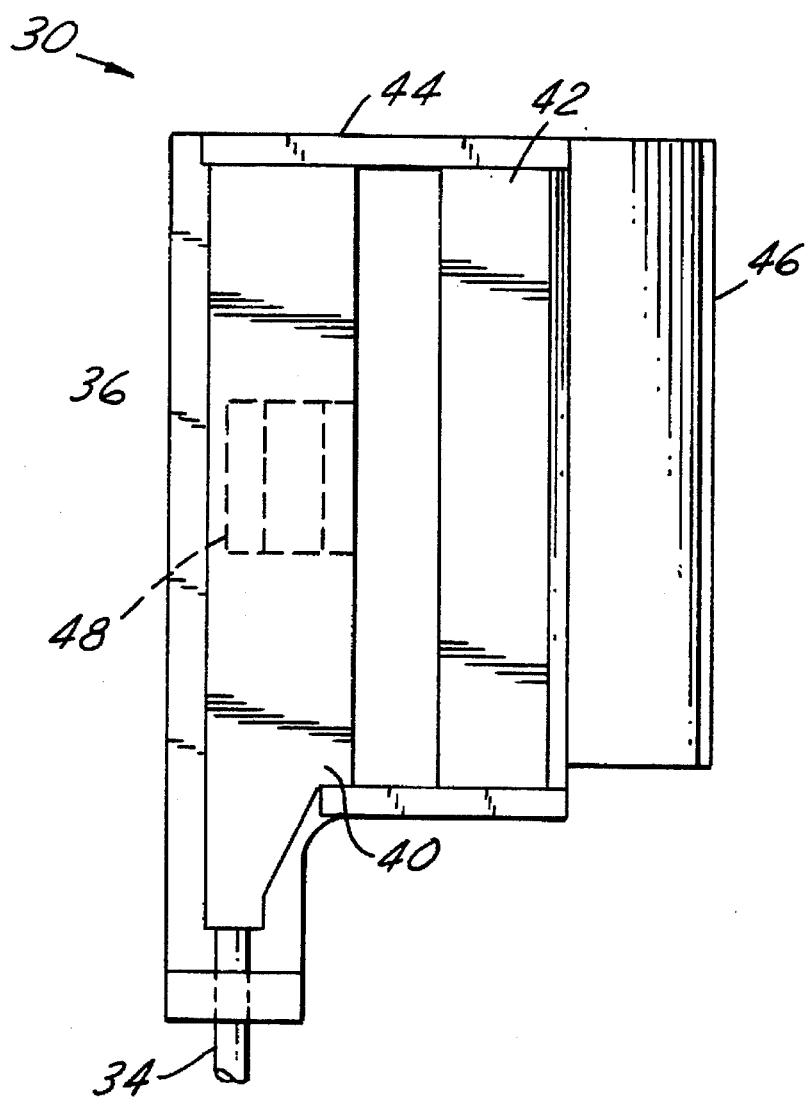
FIG. 5 is a fragmentary sectional view taken substantially along the line 5—5 in FIG. 4.

A light source 30 is positioned to one side of container 22 at station 24 for directing light energy on the container at the station. Light source 30 comprises a lamp with power supply 32 connected by a fiber-optic bundle 34 to a fiber-optic array 36. As shown in FIG. 3, fiber-optic array 36 comprises a linear essentially one-dimensional array of individual fiber-optic elements 38. Preferably, fiber-optic cable 34 feeds into a housing 40 in which the bundle is essentially fanned into a plane that is essentially one fiber-optic element thick, with the fiber-optic elements thereby terminating in the linear array illustrated in FIG. 3. Fiber-optic array 36 preferably comprises several hundred individual fiber-optic elements 38 fanned into the planar array illustrated in FIG. 3. A cylindrical lens 42 is mounted by suitable bracketry 44 (FIGS. 4 and 5) at a position spaced from enclosure 40 of fiber-optic array 36. A mirror 46 is fastened to light source bracketry 44 at an angle to lens 42 for reflecting light energy from array 36 and lens 42 through the sidewall of container 22, at which the light is focused to a narrow vertical strip as previously described. A clamp 48 is fastened to light source bracketry 44 for vertically and angularly adjusting orientation of the assembly relative to the container at inspection station 24.

A linear array camera 50 (FIG. 1) is positioned relative to container 22 at station 24 for receiving light energy from light source 30 reflected by checks in the container sidewall. Camera 50 includes a linear array of photosensitive elements oriented optically parallel to axis 23 of container 22 at inspection station 24. An information processor 52 is coupled to linear array camera 50 and container rotation mechanism 26 for scanning the elements of camera 50 at increments of container rotation, and thereby receiving from the camera image data indicative of any checks in the sidewall of container 22 that reflect light from source 30 onto the camera. Linear array camera 50, information processor 52 and container rotation mechanism 26 may be of the type disclosed in above-noted U.S. Pat. No. 4,584,469, the disclosure of which is incorporated herein by reference for purposes of background. Alternatively, camera 50 may be an area array camera of the type disclosed in U.S. Pat. No. 5,200,801 assigned to the assignee hereof.

Figure 2:
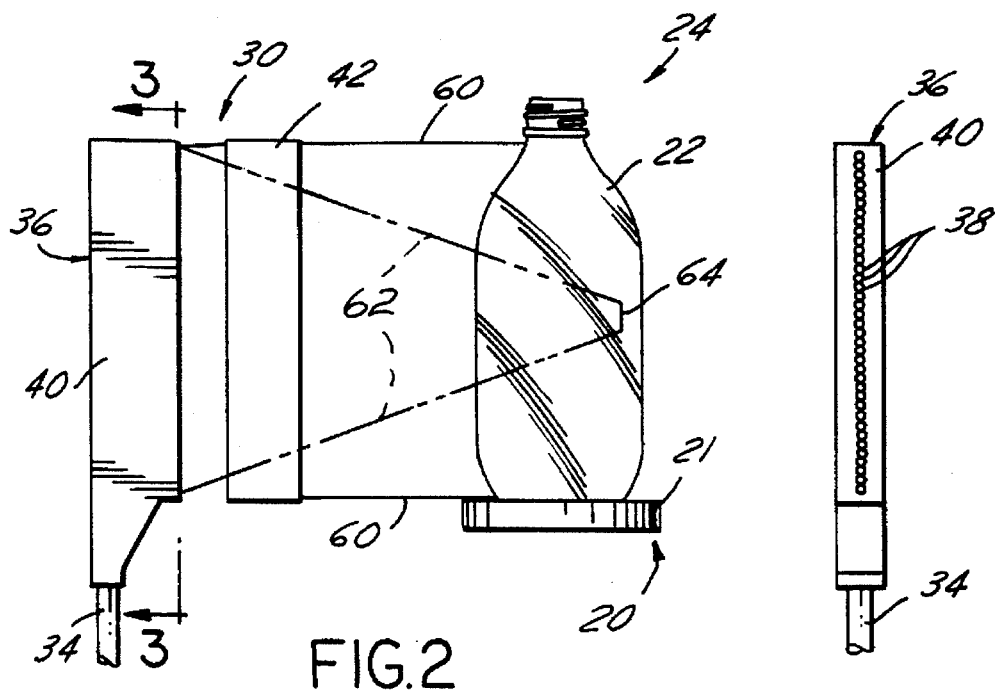
FIG. 2 is a schematic diagram of a portion of the container and a portion of the light source in the apparatus of FIG. 1.

The ends of the individual fiber-optic elements 38 function in effect as individual light sources from which light rays emerge and diverge toward cylindrical lens 42. Lens 42 functions to focus the light rays in the direction perpendicular to container axis 23, as illustrated in FIG. 1, but does not substantially affect or bend the path of travel of the individual light rays parallel to container axis 23. Thus, the light rays from the individual fiber-optic element ends diverge and intersect each other so that, when incident on the container sidewall, they travel essentially in a tightly focused plane parallel to the container axis, but intersect and illuminate the container sidewall from multiple differing angles within that plane. Thus, in FIG. 2, the overall vertical dimension of the illumination beam is illustrated by the solid lines 60, while the phantom lines 62 illustrate the angles of illumination of a split seam 64 in the sidewall of container 22. Because of the multiple differing angles at which the light is incident on split seam 64, the likelihood of detecting split seam 64 at camera 50 is greatly enhanced even if the split seam is not oriented exactly or substantially parallel to container axis 23.

We claim:

1. Apparatus for detecting vertical checks and split seams in a sidewall of a translucent container having a central axis comprising:

means for rotating the container about its central axis, a source of light for illuminating an elongated strip on the sidewall of the container in said rotating means, said strip being parallel to the container axis, in such a way that illumination rays are incident simultaneously from multiple angles at any point within said strip, a camera positioned externally of the container for receiving light reflected by vertical checks and split seams in the illuminated strip of the container sidewall, and means responsive to said camera for detecting such vertical checks and split seams in the container sidewall as a function of such reflected light.

2. The apparatus set forth in claim 1 wherein said light source comprises means for projecting an illumination beam onto the sidewall of the container in such a way that said light rays are oriented at said multiple angles essentially in a plane parallel to the container axis.

3. The apparatus set forth in claim 1 wherein said light source comprises a fiber-optic ribbon coupled at one end to a source of illumination and disposed at a second end to project said illumination beam onto said elongated strip of the container sidewall.

4. The apparatus set forth in claim 3 wherein said fiber-optic ribbon at said second end forms essentially a linear array of individual fiber-optics optically parallel to the container axis.

5. The apparatus set forth in claim 4 wherein said light source further comprises a cylindrical lens spaced from said second end of said fiber-optic ribbon for focusing light from said second end of said fiber-optic ribbon in a direction perpendicular to the container axis.

6. The apparatus set forth in claim 4 wherein said fiber-optic ribbon has a dimension parallel to the central axis of the container at least as great as the dimension of the illuminated strip of the container parallel to such axis.

7. The apparatus set forth in claim 6 wherein said light source further comprises mean for adjustably positioning said light source with respect to the container and camera.

8. The apparatus set forth in claim 1 wherein said camera comprises a linear array of light sensitive elements optically parallel to the container axis.

9. The apparatus set forth in claim 8 further comprising means for scanning said linear array of light sensitive elements at increments of container rotation.

10. A method of inspecting translucent containers comprising the steps of:

(a) illuminating an elongated strip of the sidewall of the container in such a way that illumination rays are incident at any point with the strip at multiple angles simultaneously from directions tangential to the container sidewall, (b) directing light energy reflected by vertical checks and split seams in the illuminated strip onto photosensitive means, and (c) detecting vertical checks and split seams in the container sidewall as a function of such reflected energy.

11. The method set forth in claim 10 wherein said step (a) is carried out by directing light energy onto said illuminated strip through a fiber-optic bundle in which the individual optical fibers are disposed in a linear array optically parallel to the illuminated strip.

12. The method set forth in claim 11 comprising the additional step of:

(a) rotating the container about its central axis at an orientation in which such axis is parallel to the illuminated strip on the container sidewall.

13. Apparatus for detecting checks in a translucent container having a sidewall and a central axis comprising:

a source of light for illuminating an elongated narrow strip of the container sidewall parallel to the container axis from a direction lateral to the container axis and tangential to the container sidewall in such a way that illumination rays are incident at any point within said strip from multiple angles simultaneously essentially coplanar with each other and with the strip, a camera positioned externally of the container for receiving light reflected by checks in the illuminated strip of the container sidewall along a reflective direction perpendicular to the direction of illumination of said container sidewall from said light source, and means responsive to said camera for detecting checks in the container as a function of such reflected light.

\* \* \* \* \*